US012594168B2

(12) United States Patent
Axelson, Jr. et al.

(10) Patent No.: US 12,594,168 B2
(45) Date of Patent: Apr. 7, 2026

(54) ROTARY ARC PATELLA ARTICULATING GEOMETRY

(71) Applicant: Howmedica Osteonics Corp., Mahwah, NJ (US)

(72) Inventors: Stuart L. Axelson, Jr., Succasunna, NJ (US); Robert Davignon, Morris Plains, NJ (US); Sanghita Bhattacharya, Basking Ridge, NJ (US); Michael C. Ferko, Warwick, NY (US); Peter Wellings, Somerset, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1033 days.

(21) Appl. No.: 17/114,718

(22) Filed: Dec. 8, 2020

(65) Prior Publication Data

US 2021/0085473 A1     Mar. 25, 2021

Related U.S. Application Data

(62) Division of application No. 16/170,311, filed on Oct. 25, 2018, now Pat. No. 10,893,948.

(60) Provisional application No. 62/580,575, filed on Nov. 2, 2017.

(51) Int. Cl.
  *A61F 2/38*          (2006.01)
  *A61F 2/30*          (2006.01)

(52) U.S. Cl.
  CPC .. *A61F 2/3877* (2013.01); *A61F 2002/30125* (2013.01); *A61F 2002/30878* (2013.01); *A61F*

2002/30892 (2013.01); *A61F 2002/30934* (2013.01); *A61F 2230/0008* (2013.01)

(58) Field of Classification Search
  CPC .............. A61F 2/3877; A61F 2002/648; A61F 2/3859; A61B 17/1677; A61B 17/1767
  See application file for complete search history.

(56) References Cited

U.S. PATENT DOCUMENTS

| | | |
|---|---|---|
| 3,801,989 A | 4/1974 | McKee |
| 3,806,961 A | 4/1974 | Muller |
| 3,878,566 A | 4/1975 | Bechtol |
| 3,927,423 A | 12/1975 | Swanson |
| 3,964,106 A | 6/1976 | Hutter, Jr. et al. |
| 4,007,495 A | 2/1977 | Frazier |

(Continued)

FOREIGN PATENT DOCUMENTS

| | | |
|---|---|---|
| DE | 3332354 A1 | 3/1985 |
| DE | 4221006 A1 | 1/1994 |

(Continued)

*Primary Examiner* — Brian A Dukert
(74) *Attorney, Agent, or Firm* — Lerner David LLP

(57)          ABSTRACT

Disclosed herein are patellar implants and methods to prepare bone for receiving the same. The patellar implant may include an articulating surface with an elliptically shaped median ridge. The anterior surface of the patellar implant may have a non-planar surface to engage with a resected natural patella. The non-planar surface may allow for varying thickness of the patellar implant. The patellar implant may include dual attachment features to secure patellar implant to a resected patella by onlay and inlay techniques. A method for attaching a patellar implant to a patella may include onlay and inlay techniques and may further include bone preparation at the implant-bone interface.

12 Claims, 10 Drawing Sheets

(56)  References Cited

U.S. PATENT DOCUMENTS

| | | | |
|---|---|---|---|
| 4,041,550 A | 8/1977 | Frazier | |
| 4,094,017 A | 6/1978 | Matthews et al. | |
| 4,151,615 A | 5/1979 | Hall | |
| 4,158,894 A | 6/1979 | Worrell | |
| 4,240,162 A | 12/1980 | Devas | |
| 4,285,070 A | 8/1981 | Averill | |
| 4,309,778 A | 1/1982 | Buechel et al. | |
| 4,340,978 A | 7/1982 | Buechel et al. | |
| 4,344,192 A | 8/1982 | Imbert | |
| 4,457,306 A | 7/1984 | Borzone | |
| 4,479,271 A | 10/1984 | Bolesky et al. | |
| 4,633,862 A | 1/1987 | Petersen | |
| 4,650,490 A | 3/1987 | Figgie, III | |
| 4,706,660 A | 11/1987 | Petersen | |
| 4,888,021 A | 12/1989 | Forte et al. | |
| 4,944,756 A | 7/1990 | Kenna | |
| 4,964,867 A | 10/1990 | Boger | |
| 4,979,957 A | 12/1990 | Hodorek | |
| 4,997,445 A | 3/1991 | Hodorek | |
| 5,011,496 A | 4/1991 | Forte et al. | |
| 5,019,104 A | 5/1991 | Whiteside et al. | |
| 5,021,055 A | 6/1991 | Burkinshaw et al. | |
| 5,021,061 A | 6/1991 | Wevers et al. | |
| 5,035,700 A | 7/1991 | Kenna | |
| 5,129,908 A | 7/1992 | Petersen | |
| 5,133,758 A | 7/1992 | Hollister | |
| 5,180,384 A | 1/1993 | Mikhail | |
| 5,181,924 A | 1/1993 | Gschwend et al. | |
| 5,197,986 A | 3/1993 | Mikhail | |
| 5,222,955 A | 6/1993 | Mikhail | |
| 5,236,462 A | 8/1993 | Mikhail | |
| 5,246,460 A | 9/1993 | Goodfellow et al. | |
| 5,330,532 A | 7/1994 | Ranawat | |
| 5,358,529 A | 10/1994 | Davidson | |
| 5,383,937 A | 1/1995 | Mikhail | |
| 5,395,401 A | 3/1995 | Bahler | |
| 5,425,775 A | 6/1995 | Kovacevic et al. | |
| 5,480,443 A | 1/1996 | Elias | |
| 5,514,183 A | 5/1996 | Epstein et al. | |
| 5,522,901 A | 6/1996 | Thomas et al. | |
| 5,580,353 A * | 12/1996 | Mendes | A61B 17/1767 |
| | | | 623/20.18 |
| 5,593,450 A | 1/1997 | Scott et al. | |
| 5,609,640 A | 3/1997 | Johnson | |
| 5,609,644 A | 3/1997 | Ashby et al. | |
| 5,624,462 A | 4/1997 | Bonutti | |
| 5,702,465 A | 12/1997 | Burkinshaw | |
| 5,702,467 A | 12/1997 | Gabriel et al. | |
| 5,716,360 A | 2/1998 | Baldwin et al. | |
| 5,723,016 A | 3/1998 | Minns et al. | |
| 5,725,584 A | 3/1998 | Walker et al. | |
| 5,728,162 A | 3/1998 | Eckhoff | |
| 5,871,539 A | 2/1999 | Pappas | |
| 5,871,540 A | 2/1999 | Weissman et al. | |
| 5,871,541 A | 2/1999 | Gerber | |
| 5,941,884 A | 8/1999 | Corvelli et al. | |
| 5,989,472 A | 11/1999 | Ashby et al. | |
| 6,010,509 A | 1/2000 | Delgado et al. | |
| 6,102,955 A | 8/2000 | Mendes et al. | |
| 6,146,423 A | 11/2000 | Cohen et al. | |
| 6,190,391 B1 | 2/2001 | Stubbs | |
| 6,190,415 B1 | 2/2001 | Cooke et al. | |
| 6,217,617 B1 | 4/2001 | Bonutti | |
| 6,315,798 B1 | 11/2001 | Ashby et al. | |
| 6,506,193 B1 | 1/2003 | Stubbs | |
| 6,602,292 B2 | 8/2003 | Burkinshaw | |
| 6,616,696 B1 | 9/2003 | Merchant | |
| 6,709,460 B2 | 3/2004 | Merchant | |
| 6,800,094 B2 | 10/2004 | Burkinshaw | |
| 6,802,864 B2 | 10/2004 | Tornier | |
| 6,846,329 B2 | 1/2005 | McMinn | |
| 6,855,150 B1 | 2/2005 | Linehan | |
| 6,916,341 B2 | 7/2005 | Rolston | |
| 7,208,222 B2 | 4/2007 | Rolfe et al. | |
| 7,258,701 B2 | 8/2007 | Aram et al. | |
| 7,476,250 B1 | 1/2009 | Mansmann | |
| 7,517,365 B2 | 4/2009 | Carignan et al. | |
| 7,572,295 B2 | 8/2009 | Steinberg | |
| 7,691,149 B2 | 4/2010 | Brown et al. | |
| 7,713,305 B2 | 5/2010 | Ek | |
| 7,749,276 B2 | 7/2010 | Fitz | |
| 7,758,651 B2 | 7/2010 | Chauhan et al. | |
| 7,806,896 B1 | 10/2010 | Bonutti | |
| 7,837,736 B2 | 11/2010 | Bonutti | |
| 7,972,383 B2 | 7/2011 | Goldstein et al. | |
| 8,002,839 B2 | 8/2011 | Rochetin et al. | |
| 8,062,302 B2 | 11/2011 | Lang et al. | |
| 8,092,544 B2 | 1/2012 | Wright et al. | |
| 8,105,330 B2 | 1/2012 | Fitz et al. | |
| 8,133,233 B2 | 3/2012 | Fitz | |
| 8,142,509 B2 | 3/2012 | McKinnon et al. | |
| 8,182,542 B2 | 5/2012 | Ferko | |
| 8,216,319 B2 | 7/2012 | Rhodes | |
| 8,226,725 B2 | 7/2012 | Ferko | |
| 8,268,005 B2 | 9/2012 | Brown et al. | |
| 8,282,685 B2 | 10/2012 | Rochetin et al. | |
| 8,337,501 B2 | 12/2012 | Fitz et al. | |
| 8,460,392 B2 | 6/2013 | Wright et al. | |
| 8,506,639 B2 | 8/2013 | Hayden et al. | |
| 8,545,569 B2 | 10/2013 | Fitz et al. | |
| 8,556,982 B2 | 10/2013 | Wright et al. | |
| 8,585,708 B2 | 11/2013 | Fitz et al. | |
| 8,632,552 B2 | 1/2014 | Bonutti | |
| 8,657,827 B2 | 2/2014 | Fitz et al. | |
| 8,682,052 B2 | 3/2014 | Fitz et al. | |
| 8,690,945 B2 | 4/2014 | Fitz et al. | |
| 8,696,754 B2 | 4/2014 | Cuckler et al. | |
| 8,747,478 B2 | 6/2014 | Ries et al. | |
| 8,808,386 B2 | 8/2014 | Engh et al. | |
| 8,814,946 B2 | 8/2014 | Steinberg | |
| 8,834,574 B2 * | 9/2014 | Todd | A61F 2/3877 |
| | | | 623/20.18 |
| 8,888,858 B2 | 11/2014 | Brown et al. | |
| 8,945,135 B2 | 2/2015 | Ries et al. | |
| 8,961,529 B2 | 2/2015 | Carignan et al. | |
| 8,986,306 B2 | 3/2015 | Wright et al. | |
| 9,023,050 B2 | 5/2015 | Lang et al. | |
| 9,078,676 B2 | 7/2015 | Randle et al. | |
| 9,078,772 B2 | 7/2015 | Jones et al. | |
| 9,107,680 B2 | 8/2015 | Fitz et al. | |
| 9,125,749 B2 | 9/2015 | Amirouche et al. | |
| 9,138,241 B2 | 9/2015 | Kuczynski | |
| 9,138,322 B2 | 9/2015 | Wright et al. | |
| 9,180,015 B2 | 11/2015 | Fitz et al. | |
| 9,186,161 B2 | 11/2015 | Lang et al. | |
| 9,186,254 B2 | 11/2015 | Fitz et al. | |
| 9,289,305 B2 | 3/2016 | Dacus | |
| 9,314,342 B2 | 4/2016 | Andriacchi et al. | |
| 9,333,085 B2 | 5/2016 | Fitz et al. | |
| 9,381,085 B2 | 7/2016 | Axelson, Jr. et al. | |
| 9,393,124 B2 | 7/2016 | Angibaud | |
| 9,486,321 B1 | 11/2016 | Smith et al. | |
| 9,498,342 B2 | 11/2016 | Wright et al. | |
| 9,554,813 B2 | 1/2017 | Clever et al. | |
| 9,572,672 B2 | 2/2017 | Sharkey | |
| 11,026,796 B2 * | 6/2021 | Mistry | A61F 2/2846 |
| 2001/0023371 A1 | 9/2001 | Bonutti | |
| 2002/0058948 A1 | 5/2002 | Arlettaz | |
| 2003/0033018 A1 | 2/2003 | Merchant | |
| 2003/0083751 A1 | 5/2003 | Tornier | |
| 2003/0088315 A1 | 5/2003 | Supinski | |
| 2003/0120346 A1 | 6/2003 | Mercinek et al. | |
| 2003/0181984 A1 | 9/2003 | Abendschein | |
| 2004/0143336 A1 | 7/2004 | Burkinshaw | |
| 2004/0143338 A1 | 7/2004 | Burkinshaw et al. | |
| 2004/0162561 A1 | 8/2004 | Marchyn et al. | |
| 2004/0236428 A1 | 11/2004 | Burkinshaw et al. | |
| 2004/0247641 A1 | 12/2004 | Felt et al. | |
| 2004/0254645 A1 | 12/2004 | Arnin et al. | |
| 2005/0143830 A1 | 6/2005 | Marcinek et al. | |
| 2005/0143833 A1 | 6/2005 | Merchant | |
| 2005/0171612 A1 | 8/2005 | Rolston | |
| 2005/0246028 A1 | 11/2005 | Pappas et al. | |
| 2006/0052792 A1 | 3/2006 | Boettiger et al. | |

(56)  References Cited

U.S. PATENT DOCUMENTS

| | | |
|---|---|---|
| 2007/0100447 A1 | 5/2007 | Steinberg |
| 2007/0100460 A1 | 5/2007 | Rhodes |
| 2007/0100461 A1 | 5/2007 | Incavo et al. |
| 2007/0100462 A1 | 5/2007 | Lang et al. |
| 2007/0123991 A1 | 5/2007 | Steinberg |
| 2007/0162142 A1 | 7/2007 | Stone |
| 2007/0173858 A1 | 7/2007 | Engh et al. |
| 2008/0243258 A1 | 10/2008 | Sancheti |
| 2009/0005708 A1 | 1/2009 | Johanson et al. |
| 2009/0036993 A1 | 2/2009 | Metzger |
| 2009/0222103 A1 | 9/2009 | Fitz et al. |
| 2009/0259317 A1 | 10/2009 | Steinberg |
| 2010/0070046 A1 | 3/2010 | Steinberg |
| 2010/0160915 A1 | 6/2010 | Chauhan et al. |
| 2010/0174379 A1 | 7/2010 | McMinn |
| 2010/0280624 A1 | 11/2010 | Engh et al. |
| 2010/0312342 A1 | 12/2010 | Ek |
| 2011/0144760 A1 | 6/2011 | Wong et al. |
| 2011/0224801 A1 | 9/2011 | Mansmann |
| 2012/0010623 A1 | 1/2012 | Bonutti |
| 2012/0059485 A1 | 3/2012 | Roger |
| 2012/0116525 A1 | 5/2012 | Brown et al. |
| 2012/0136451 A1 | 5/2012 | Fitz |
| 2012/0165821 A1 | 6/2012 | Carignan et al. |
| 2012/0197408 A1 | 8/2012 | Lang et al. |
| 2012/0209393 A1* | 8/2012 | Ries ..................... A61F 2/3877 |
| | | 623/20.2 |
| 2012/0209395 A1 | 8/2012 | Tepic et al. |
| 2012/0245699 A1 | 9/2012 | Lang et al. |
| 2013/0165939 A1 | 6/2013 | Ries et al. |
| 2013/0166035 A1 | 6/2013 | Landon |
| 2013/0226185 A1 | 8/2013 | Bonutti |
| 2014/0094813 A1 | 4/2014 | Clever et al. |
| 2014/0094819 A1 | 4/2014 | Clever et al. |
| 2014/0128973 A1 | 5/2014 | Howard et al. |
| 2014/0142713 A1 | 5/2014 | Wright et al. |
| 2014/0142714 A1 | 5/2014 | Wright et al. |
| 2014/0228964 A1 | 8/2014 | Lew et al. |
| 2014/0277523 A1 | 9/2014 | Masini et al. |
| 2014/0358241 A1 | 12/2014 | Afriat |
| 2015/0005772 A1 | 1/2015 | Anglin et al. |
| 2015/0196325 A1 | 7/2015 | Shenoy et al. |
| 2016/0030182 A1 | 2/2016 | McMinn |
| 2016/0045321 A1 | 2/2016 | Gabriel et al. |
| 2016/0081758 A1 | 3/2016 | Bonutti |
| 2016/0192878 A1 | 7/2016 | Hunter |
| 2016/0206331 A1 | 7/2016 | Fitz et al. |
| 2016/0235541 A1 | 8/2016 | Samuelson et al. |
| 2016/0242915 A1 | 8/2016 | Samuelson et al. |
| 2016/0242916 A1 | 8/2016 | Samuelson et al. |
| 2016/0242918 A1 | 8/2016 | Samuelson et al. |
| 2016/0242919 A1 | 8/2016 | Engh et al. |
| 2016/0256280 A1 | 9/2016 | Trauner |
| 2016/0256283 A1 | 9/2016 | Samuelson et al. |
| 2016/0256284 A1 | 9/2016 | Fitz et al. |
| 2016/0278794 A1 | 9/2016 | Boldt et al. |
| 2016/0324646 A1 | 11/2016 | Carignan et al. |
| 2016/0367373 A1 | 12/2016 | Samuelson et al. |
| 2017/0007414 A1 | 1/2017 | Fitz et al. |
| 2018/0193168 A1 | 7/2018 | Termanini et al. |
| 2020/0138457 A1 | 5/2020 | Lorean et al. |
| 2022/0117613 A1 | 4/2022 | Collazo |
| 2023/0404598 A1 | 12/2023 | Steeven |

FOREIGN PATENT DOCUMENTS

| | | |
|---|---|---|
| EP | 0307654 A2 | 3/1989 |
| EP | 0437173 A1 | 7/1991 |
| EP | 0676182 A1 | 10/1995 |
| EP | 1308142 A2 | 5/2003 |
| EP | 2471494 A1 | 7/2012 |
| EP | 2572678 A1 | 3/2013 |
| EP | 2675399 A1 | 12/2013 |
| EP | 2712588 A1 | 4/2014 |
| FR | 2440185 A1 | 5/1980 |
| FR | 2615096 A1 | 11/1988 |
| FR | 2642301 A1 | 8/1990 |
| FR | 2652497 A1 | 4/1991 |
| FR | 2682590 A1 | 4/1993 |
| FR | 2700260 A1 | 7/1994 |
| FR | 2746632 A1 | 10/1997 |
| FR | 2884408 A1 | 10/2006 |
| FR | 2976176 A1 | 12/2012 |
| FR | 2997625 A1 | 5/2014 |
| GB | 1522497 A | 8/1978 |
| GB | 2301032 A | 11/1996 |
| GB | 2433698 A | 7/2007 |
| GB | 2461149 A | 12/2009 |
| JP | 5465475 B2 | 4/2014 |
| WO | 9300871 A1 | 1/1993 |
| WO | 9522303 A2 | 8/1995 |
| WO | 9725006 A1 | 7/1997 |
| WO | 03068119 A2 | 8/2003 |
| WO | 2014159919 A1 | 10/2014 |
| WO | 2016026007 A1 | 2/2016 |

* cited by examiner

ROTARY ARC PATELLA ARTICULATING GEOMETRY

CROSS-REFERENCE TO RELATED APPLICATIONS

This application is a divisional of U.S. application Ser. No. 16/170,311, filed on Oct. 25, 2018, which claims the benefit of the filing of U.S. Provisional Patent Application No. 62/580,575, filed Nov. 2, 2017, the disclosure of which is hereby incorporated herein by reference.

FIELD OF INVENTION

The present invention relates to medical implants for bone and methods for bone preparation, and in particular to patellar implants and methods for preparing bone to receive the same.

BACKGROUND OF THE INVENTION

Patella resurfacing is routinely performed for treatments of various knee ailments including arthritis. After resurfacing the patella, a surgeon may implant a patellar implant on the resurfaced patella. The patellar implant generally has a patella contacting surface for engaging the resurfaced patella and an opposite surface that articulates with a distal end of a femoral body. The articulating surface of the patellar implant may be anatomically or symmetrically shaped to guide articulation of the patellar implant with the trochlear groove of the femoral body. A properly sized and configured articulating surface is preferable to ensure proper patellofemoral kinematics during weight-bearing and non-weight-bearing knee extensions.

Patellar implants with symmetric articulating designs may provide axial rotational freedom to allow for patellofemoral articular alignment. However, this design does not accurately replicate natural patellar articulating geometry. Patellar implants with anatomically shaped articulating designs may have a median ridge that is similar to the natural patella and may allow these patellar implants to closely replicate natural patellar articulating geometry. However, aligning the median ridge of the anatomically shaped articulating patellar implants with the native femoral trochlear groove may be challenging, and this design may not provide required axial rotational freedom. Even if aligned properly, the median ridge-trochlear groove alignment is generally difficult to maintain.

Bone interfacing geometries between the patellar implant and the resected patella generally consist of simple planar shapes because of the complexities of resecting patellar bone. Simple planar shapes limit patella implant design and may prevent patellar implant designs with varying thickness. For example, increasing the thickness of the patellar implant in regions of high mechanical stress and decreasing the thickness of the patellar implant in regions where maximizing bone preservation is desired are generally not possible on account of the simple planar shapes at the bone interfacing surfaces.

Patellar implants are typically secured to a resected patella surface by either an onlay or an inlay technique. An onlay technique utilizes fixation features such as posts extending from the patellar implant which are received in corresponding recesses on the resected patella surface. Onlay technique, however, may require extensive patellar bone removal. An inlay technique is performed by resecting a footprint of the patellar implant on the resecting surface and press-fitting the patellar implant into this recess. While the inlay technique may require less patellar bone removal, the patellar implant may not be embedded deep enough into the patella to provide the same level of fixation as achieved by utilizing an onlay technique. Further, the inlay technique may result in sharp, jagged bone fragments along the interface with the patellar implant and may consequently damage the patellar implant.

Therefore, there exists a need for improved patellar implants and methods for attaching the same to prepared bone.

BRIEF SUMMARY OF THE INVENTION

Disclosed herein are patellar implants and methods for securing the same to a resected patella and accompanying bone preparation methods.

In a first aspect of the present invention, a patellar implant with an anatomically shaped articular surface is provided. The patellar implant may have an anterior surface to engage with a resected interior portion of a patellar bone. A posterior articulating surface of the patellar implant may correspond to a femoral body. The articulating surface may include a median ridge portion extending posteriorly to and disposed between a lateral portion and a medial portion. The median ridge portion may extend along a first length in a superior to inferior direction and along a second length in a medial to lateral direction of the articulating surface. The first length may be greater than the second length.

In accordance with the first aspect, the median ridge portion may be substantially elliptical in shape. The first length of the median ridge may be a major axis and the second length of the median ridge may be a minor axis of the elliptical median ridge respectively. The major axis may define a boundary between a medial side and a lateral side of the median ridge. The medial side may have one or more curves defined by a curve center located laterally to the major axis and the lateral side may have one or more curves defined by a curve center located medially to the major axis.

In other aspects, a contact area of the median ridge with the femoral body may be substantially the same when the patellar implant is rotated in a medial-lateral plane. A contact surface profile of the median ridge with the femoral body may be substantially the same when the patellar implant is rotated in a medial-lateral plane.

In a second aspect of the present invention, a patellar implant with a non-planar anterior surface is provided. The patellar implant may include a posterior surface for engaging a femoral body. An anterior surface of the patellar implant may engage a patella. At least a portion of the anterior surface may be non-planar. A thickness of the patellar implant may vary at least along one axis in a medial-lateral or a superior-inferior direction. The thickness may be defined by a distance between the anterior and posterior surfaces.

In other aspects, the anterior surface may define a convex profile along a superior-inferior axis. The implant thickness may be greatest at a central region of the superior-inferior axis.

In still other aspects, the anterior surface may define a concave profile along a medial-lateral axis. The anterior surface may further define a convex profile along a superior-inferior axis.

In a third aspect of the present invention, a patellar implant with an anatomically shaped articular surface and a non-planar anterior surface is provided. The patellar implant may have an anterior surface for engaging a patellar. At least a portion of the anterior surface may be non-planar such that a thickness of the patellar implant may vary at least along one axis in a medial-lateral or a superior-inferior direction. The thickness may be defined by a distance between the anterior and posterior surfaces. The patellar implant may have a posterior articulating surface for engaging a femoral body. The articulating surface may include a median ridge portion disposed between a lateral portion and a medial portion of the patellar implant. The median ridge portion may be substantially elliptical in shape and extend along a first length in superior-inferior direction and along a second length in a medial-lateral direction of the articulating surface. The first length may be larger than and transverse to the second length.

A fourth aspect of the present invention is a method for sizing a patient-specific implant to maximize bone preservation. A method in accordance with this aspect of the invention may include the steps of obtaining an image of a patella, determining the implant thickness and providing an implant. The thickness of the patellar implant may be based on preserving patella bone. An anterior surface of the implant may be non-planar with a thickness that may vary at least along one axis in a medial-lateral or superior-inferior direction to match required implant thickness. The thickness may be defined by a distance between the anterior and posterior surfaces.

In a fifth aspect of the present invention, a patellar implant with dual attachment features is provided. An anterior surface of the patellar implant may engage with a patella. A posterior articulating surface may engage with a femoral body. One or more peripheral walls may extend between the anterior surface and the posterior surface. At least one post may extend from the anterior surface to engage with at least one opening on the patella. A first portion of the peripheral wall may be countersunk within the patellar and a second portion of the peripheral wall may extend way from the patella when the patellar implant is engaged with the patella by the post.

A sixth aspect of the present invention is a method for implanting a patellar implant. A method in accordance with this aspect of the invention may include the steps of resecting a posterior surface of a patella, removing patellar bone on resecting surface to create a recess, removing patellar bone from a surface of the recess to create one or more openings and placing the anterior surface of the patellar implant on the recess of the patella. The resection surface may correspond to the anterior surface of a patellar implant as described in the fifth aspect of the present invention. The recess on the resection surface may correspond to the footprint of the anterior surface of the patellar implant. A depth of the recess may be less than a height of one or more peripheral walls of the patellar implant. The footprint of the recess may be substantially the same or smaller than the footprint of the anterior surface. The patellar implant may be secured in the recess. The one or more openings may receive the one or more posts extending from the anterior surface of the patellar implant. One or more post the patellar implant may be received in the corresponding openings when the anterior surface of the patellar implant is placed on the recess of the patella. The patellar implant may be secured in the recess such that a first portion of the peripheral wall may be countersunk within the patella and a second portion of the peripheral wall may extends away from the wall when the anterior surface of the patellar implant is placed on the recess of the patella.

In other aspects, edges of the recess may be machined to remove bone fragments to provide smooth implant-bone interfaces. The smooth implant-bone transition may form an articulating surface. The patellar implant may be secured to the recess by press-fitting or cementing the patellar implant to the recess.

BRIEF DESCRIPTION OF THE DRAWINGS

A more complete appreciation of the subject matter of the present invention and the various advantages thereof may be realized by reference to the following detailed description, in which reference is made to the following accompanying drawings.

DETAILED DESCRIPTION

In describing preferred embodiments of the disclosure, reference will be made to directional nomenclature used in describing the human body. It is noted that this nomenclature is used only for convenience and that it is not intended to be limiting with respect to the scope of the invention.

As used herein, when referring to bones or other parts of the body, the term "anterior" means toward the front part or the face and the term "posterior" means toward the back of the body. The term "medial" means toward the midline of the body and the term "lateral" means away from the midline of the body. The term "superior" means closer to the heart and the term "inferior" means more distant from the heart.

Figure 1:
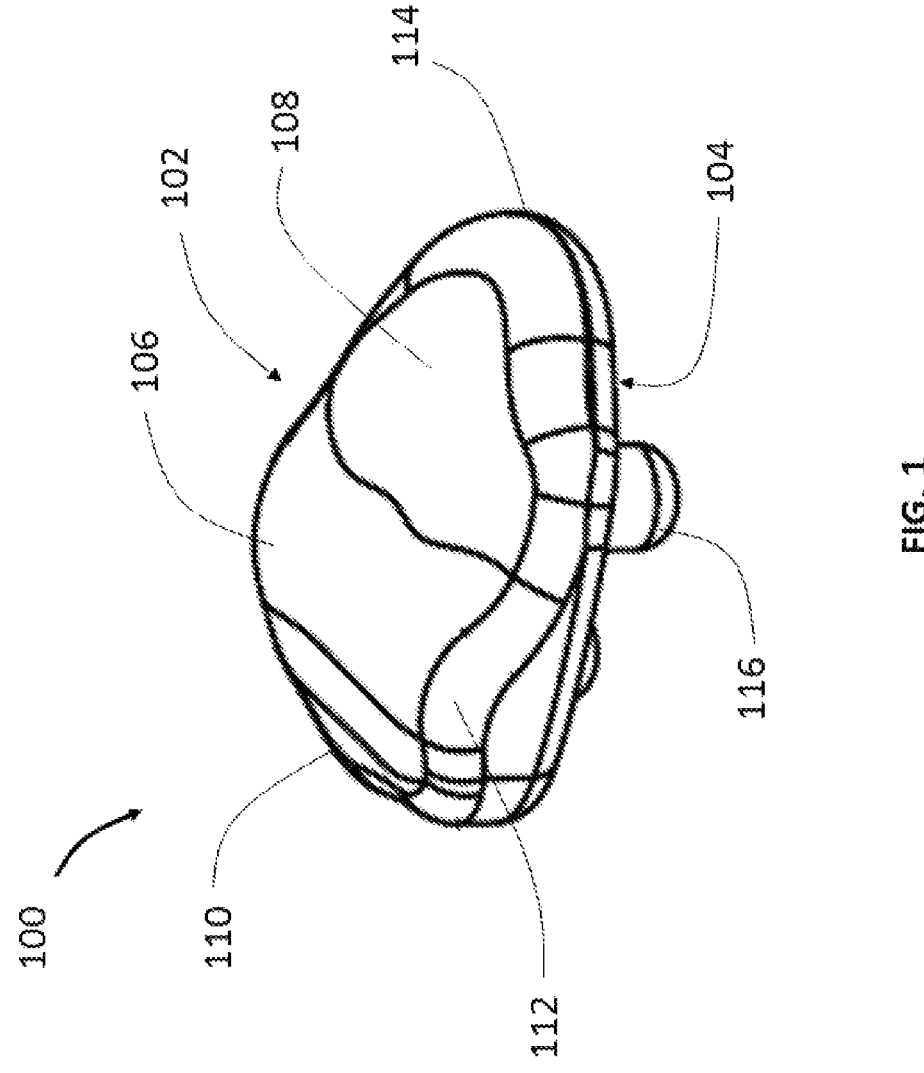
FIG. 1 is a perspective view of a patellar implant according to a first embodiment of the present invention.
Figures 2, 3:
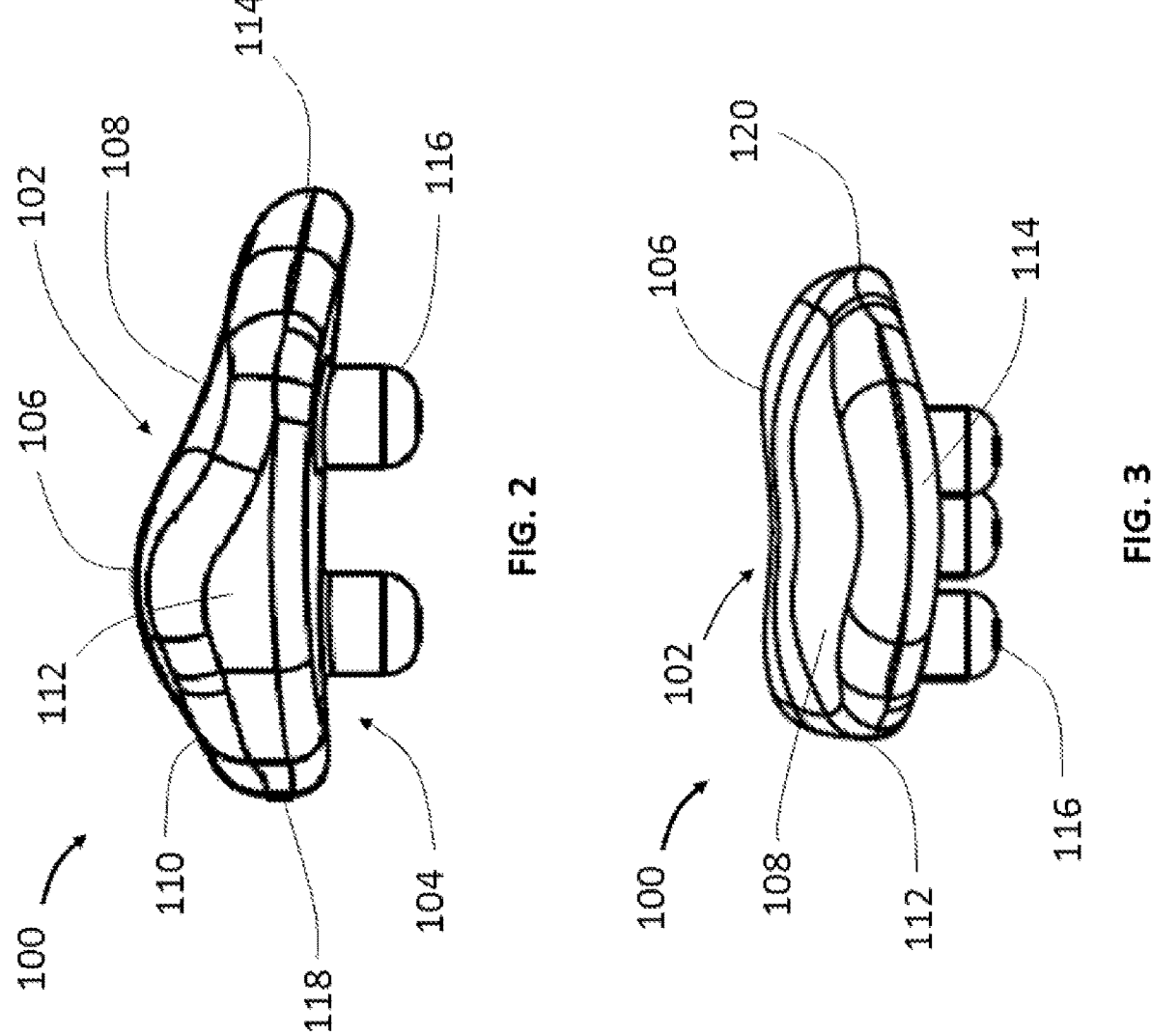
FIG. 2 is a front view of the patellar implant of FIG. 1.
FIG. 3 is a side view of the patellar implant of FIG. 1.

Referring now to FIGS. 1, 2 and 3, there is shown a patellar implant 100 in different views. Patellar implant 100 includes an articulating posterior surface 102 and an opposite anterior surface 104. Posterior surface 102 articulates with a distal end portion of a femoral body (not shown), whereas the anterior surface can be secured to a resected patella (not shown). Posterior surface 102 is anatomically shaped to match contours of the articulating surface of a natural patella and thereby replicates natural patellofemoral kinematics during flexion and extension. Posterior surface 102 has a central median ridge 106 located between a lateral facet 108 and a medial facet 110. Median ridge 106 has a convex profile when viewed in inferior-superior direction as best shown in FIG. 2 and a concave profile when viewed in medial-lateral direction as best in FIG. 3.

Lateral facet 108 and medial facet 110 are contoured to match the anatomy of the corresponding articulating surface of a trochlear groove of a femoral implant (not shown), whereby lateral facet 108 is a generally concave surface in an anterior-superior direction and also concave in a medial-lateral direction. Similarly, medial facet 110 is also generally concave in an anterior-superior direction and also concave in a medial-lateral direction as best seen in FIGS. 2 and 3. The contoured lateral and medial facet ensure that proper contact area between patellar implant 100 and the femoral implant is maintained when the patellar implant is rotated within the trochlear groove of the femoral implant. Consequently, if the trochlear implant of the femoral implant (not shown) corresponds to the shape of a natural patella, lateral face 108 and medial facet 110 contours will match the articulating profile of the natural patella. A base 112, a lateral peripheral edge 114, a medial peripheral edge 118 and an apex 120 form the peripheral walls of patellar implant 100 as best shown in FIGS. 1 and 2.

Figure 4:
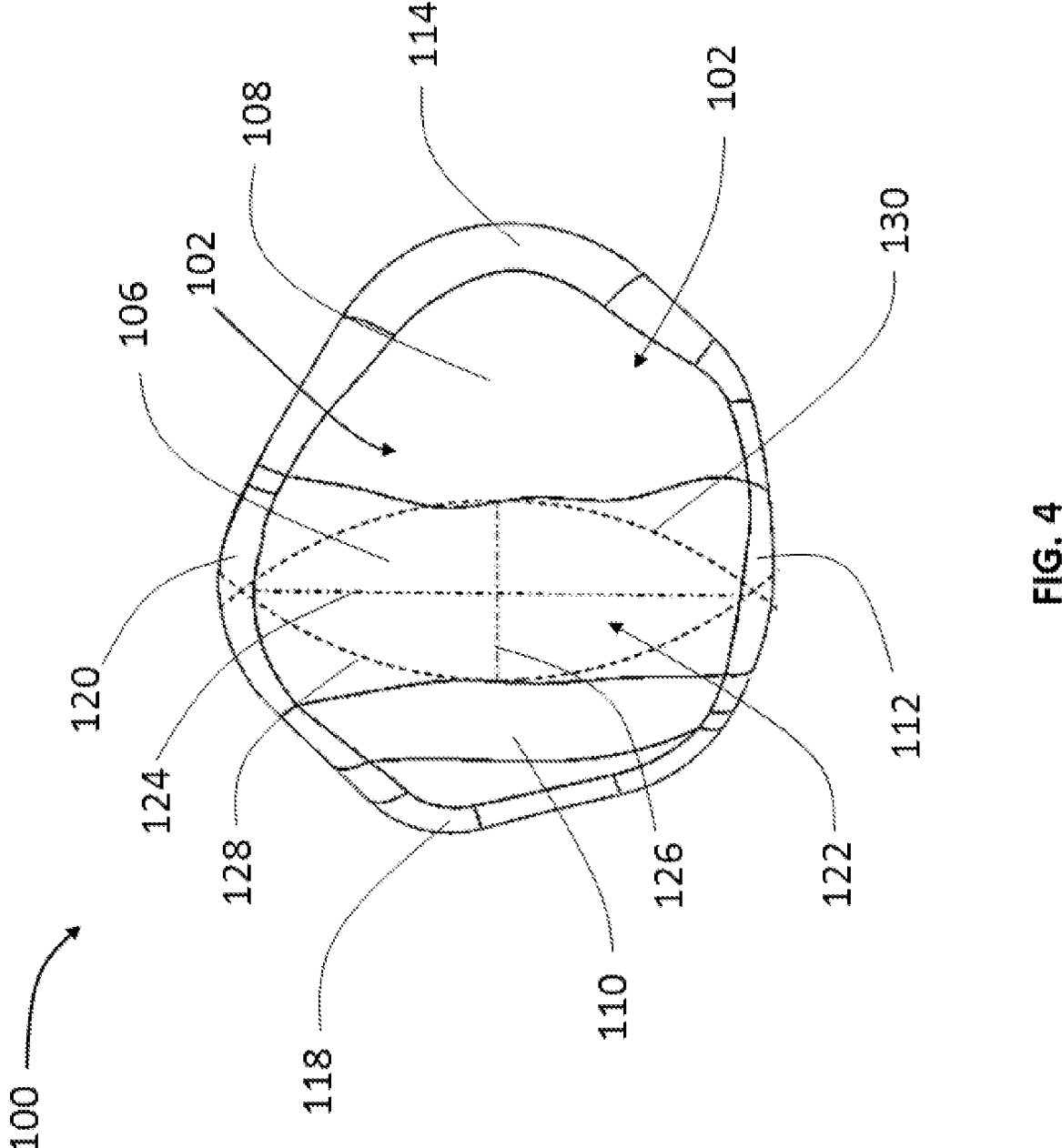
FIG. 4 is a top view of the patellar implant of FIG. 4.
Figure 5:
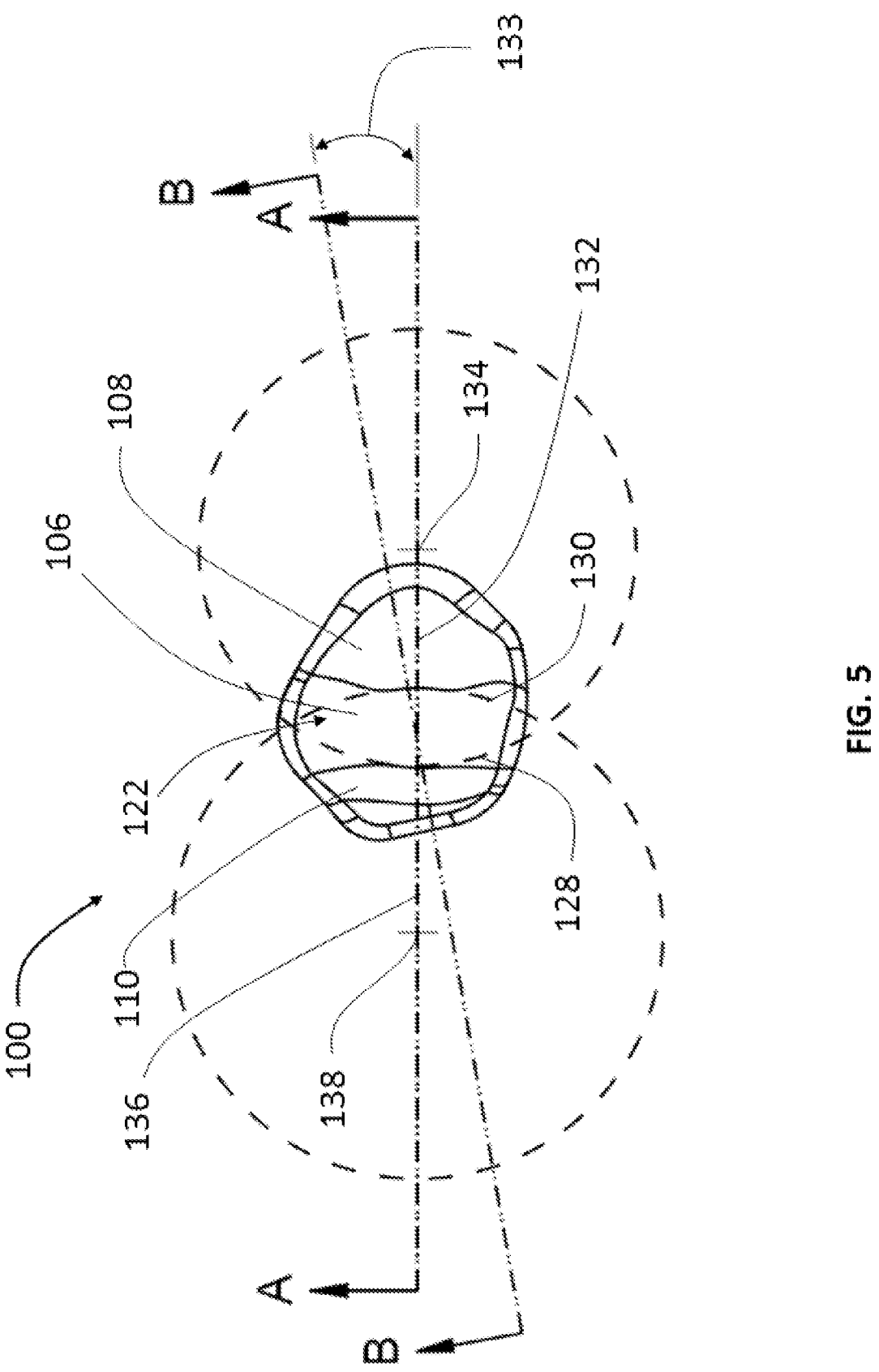
FIG. 5 is another top view of the patellar implant of FIG. 1.

FIGS. 4 and 5 show top views of patellar implant 100. Median ridge 106 has a substantially elliptical-shaped portion 122 bounded by a medial curve 128 on the medial side and a lateral curve 130 on the lateral side. Medial curve 128 and lateral curve 130 intersect at or near apex 120 and base 112. A major axis 124 of elliptical-shaped portion 122 runs from apex 120 to base 112 in a superior-inferior direction, and a minor axis of elliptical-shaped portion 122 runs medial-laterally as best shown in FIG. 4. Major axis 124 is transverse to minor axis 122 and intersects the minor axis around the center of median ridge 106. As best seen in FIG. 5, medial curve 128 has a radius 132 with a center 134 located on a lateral side of patellar implant 100. Lateral curve 130 has a radius 136 with a center 138 located on a medial side of the patellar implant 100. Major axis 124 divides elliptical-shaped portion into two regions with a lateral side having a series of curves running from an inferior to a superior direction along lateral curve 130 and a medial side having a series of curves running from an inferior to a superior direction along medial curve 128. This series of curves in conjunction with the raised central region of median ridge as best seen in FIG. 2, render the elliptical-portion with a substantially football-shaped configuration.

Figures 6, 7:
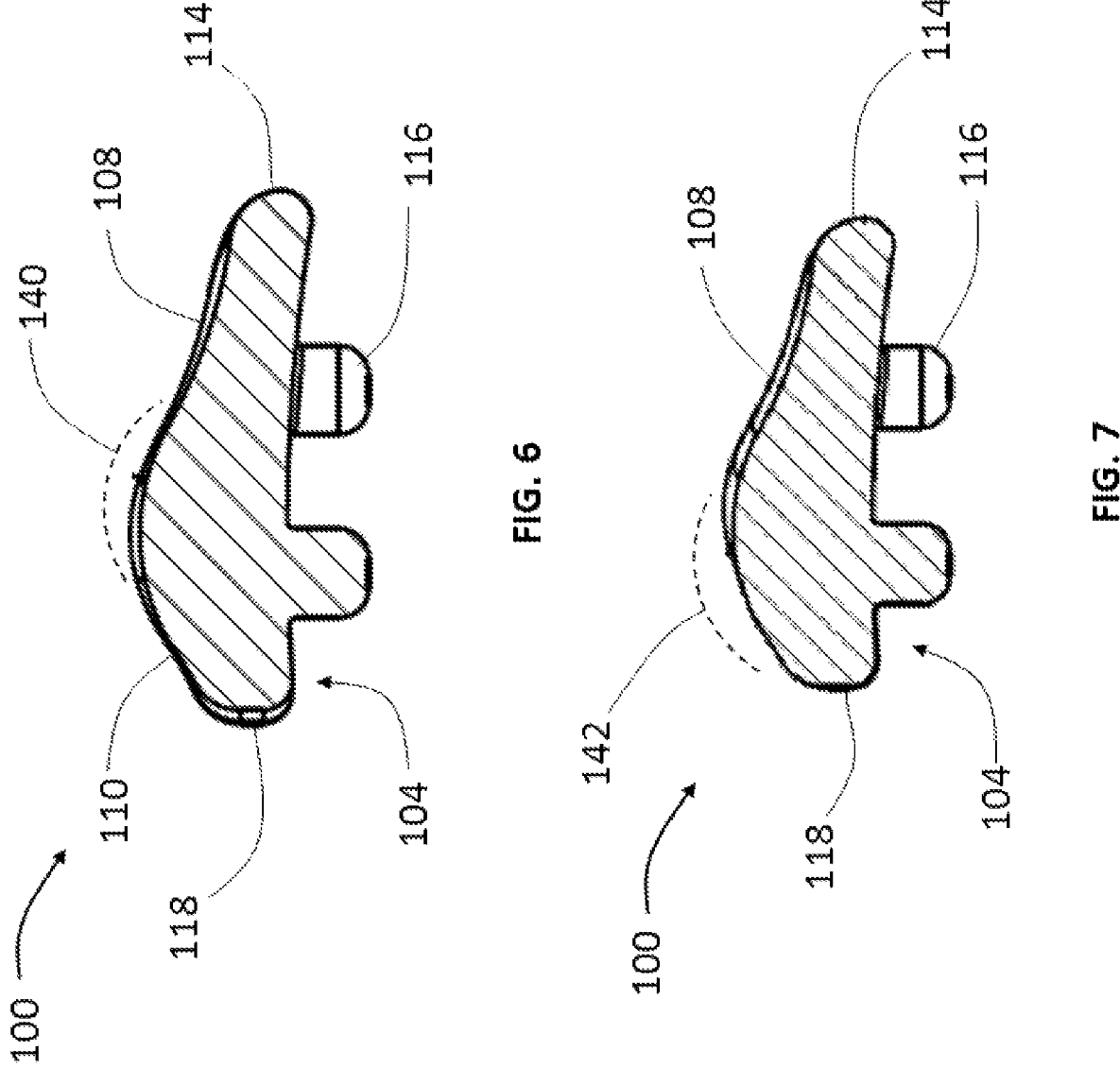
FIG. 6 is a cross-sectional view along line A-A of the patellar implant of FIG. 5.
FIG. 7 is a cross-sectional view along line B-B of the patellar implant of FIG. 5.

FIG. 6 shows a cross-sectional view of patellar implant 100 along line A-A shown in FIG. 5. Line A-A is aligned with minor axis 126 and divides patellar implant 100 into superior and inferior sections. FIG. 7 shows a second cross-sectional view of patellar implant 100 along line B-B shown in FIG. 5. Line B-B is rotated along a coronal plane in a superior-inferior direction as indicated by rotational arrow 133. A lateral curvature 140 shown in FIG. 6 on a lateral side of median ridge 106 is similar to a medial curvature 142 shown in FIG. 7 on a medial side of median ridge 106. Therefore, even when patellar implant 100 is axially rotated along a coronal plane with reference to a femoral body, the contact surface and profile, i.e., radius of curvature 140, 142, remains constant. Thus, elliptical-shaped portion 122 ensures that the natural patellofemoral kinematics is maintained with patellar implant 100 during knee flexion and extension. Further, once the elliptical-shaped portion 122 of median ridge 106 is seated in the trochlear groove of a natural patella (not shown), the elliptical-shape portion ensures that patellar implant 100 remains securely aligned with the trochlear groove through flexion and extension of the knee. The concave surface of median ridge 106 as viewed from a superior-inferior direction can be configured to allow for varying rotation of patellar implant as indicated by rotation arrow 133 to ensure that patellofemoral contact replicates the natural patellar kinematics. For example, a larger radius for medial curve 128 and lateral curve 130 will allow for greater radial rotation of patellar component 100 with respect to a femoral body in a coronal plane while maintaining providing uniform patella contact with the femoral body.

Figure 9:
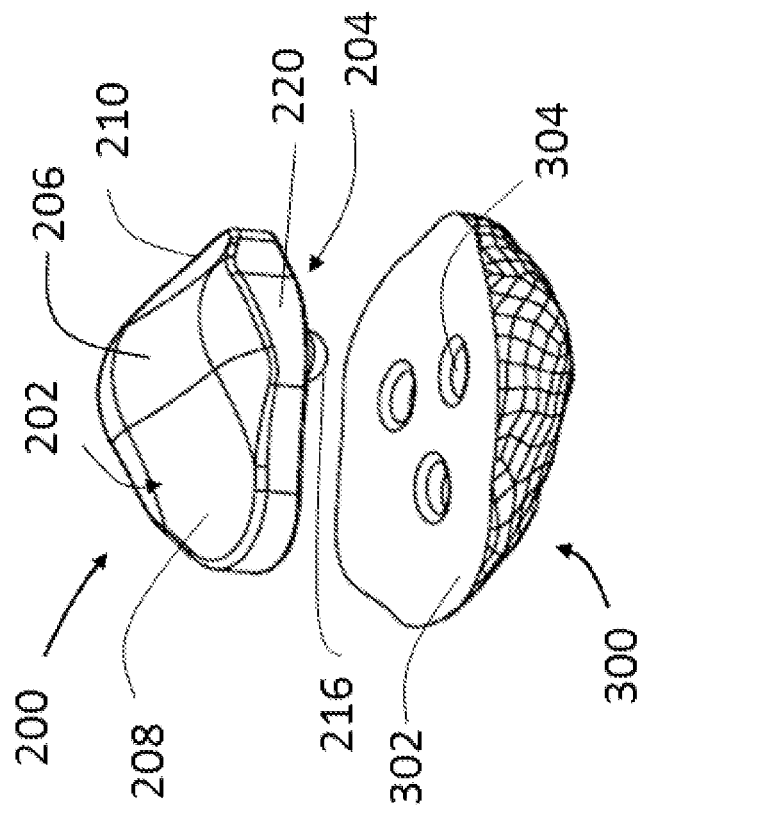
FIG. 9 is an exploded perspective view of the patellar implant and resected patella of FIG. 8.
Figure 8:
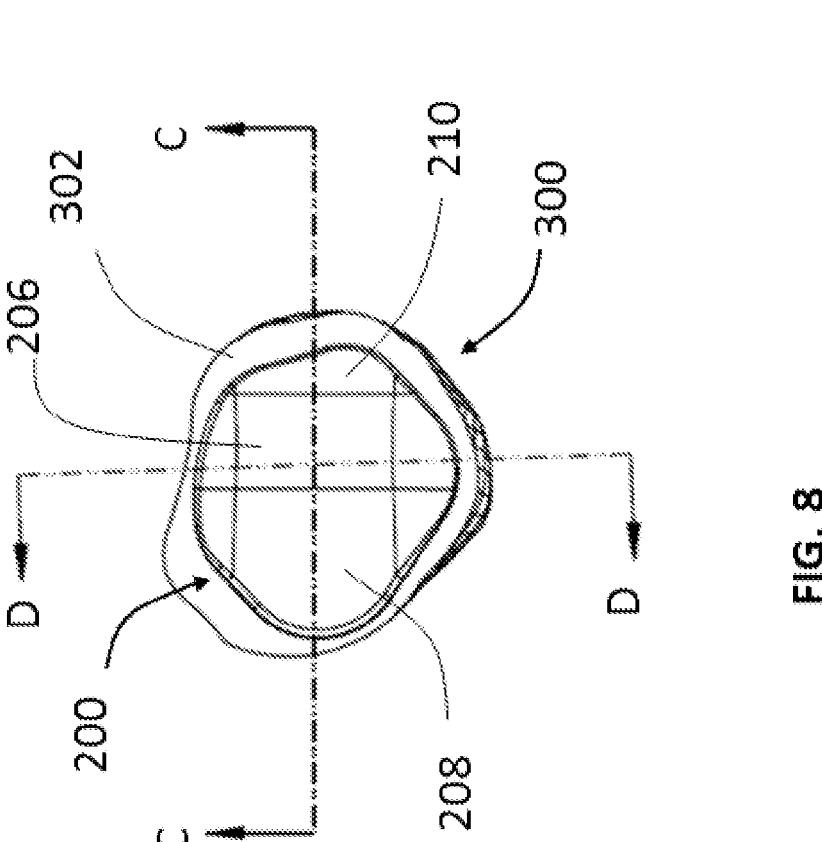
FIG. 8 is a top assembled view of a patellar implant coupled to a resected patella according to another embodiment of the present invention.

Referring now to FIGS. 8 and 9, there is shown a patellar implant 200 according to a second embodiment of the present invention. Patellar implant 200 has a posterior articulating surface 202 contoured to match the articulating surface of a natural patella. Articulating surface 202 includes a median ridge 206 between a lateral facet 208 and a median facet 210. An anterior surface 204 contoured to match a resected patella surface 302 of a patella 300 includes one or more posts 216. Posts 216 are received in corresponding recesses 304 located on resected patella surface 302 as best shown in FIG. 9. As best shown in FIG. 8, anterior surface 204 of patellar implant 200 is smaller than resected patella surface 302 leading to patellar implant undercap. Other embodiments may have patellar implants that are larger than the resected patella surface resulting in patellar implant overhang.

Figures 10, 11:
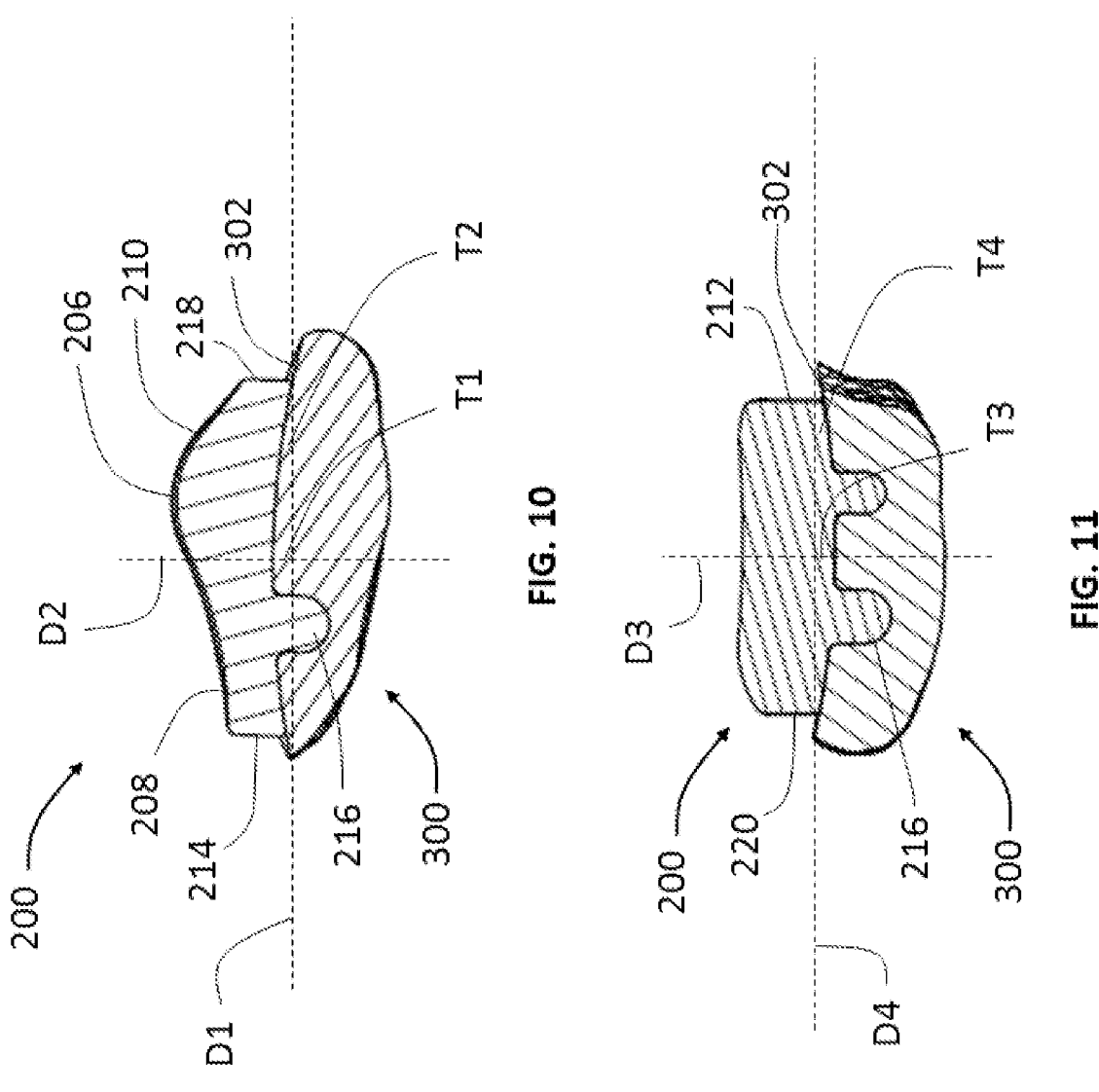
FIG. 10 is a cross-sectional view along line C-C of the patellar implant and resected patella of FIG. 9.
FIG. 11 is a cross-sectional view along line D-D of the patellar implant and resected patella of FIG. 9.

FIG. 10 is a cross-sectional view of patellar implant 200 along line C-C. Articulating surface 202 of patellar implant 200 has a concave profile in a medial-lateral direction moving from a lateral peripheral edge 214 to a medial peripheral edge 218. Consequently, resected patella 300 has a convex profile in a medial-lateral direction. Patellar thickness defined by a line D1 representing a planar surface in a coronal plane and resected patella surface 302 is greatest at a center D2 as shown by a thickness T1 and reduces towards the medial and lateral edges as indicated by a second thickness T2. Hence, non-planar patellar implant-patella interface allows for patellar implant 200 and patella 300 to have variable thickness.

FIG. 11 shows a second cross-sectional view of patellar implant 200 along line D-D of FIG. 9. Articulating surface 202 of patellar implant 200 has a convex profile in superior-inferior direction moving from an apex 220 to a base 212 of the patellar implant. Patellar implant thickness defined by a line D4 representing a planar surface in a coronal plane and articulating surface 202 is greatest at a center D3 as shown by a thickness T3 and reduces towards apex 220 and base 212 as indicated by a second thickness T4. Whereas traditional patellar implant are thinnest at the medial-lateral edges, the thickened peripheral edges 214, 218 of patellar implant 200 in a medial-lateral direction provide increased implant strength and prevent implant wear and fracture. Furthermore, the reduced thickness of patellar implant 200 at peripheral edges 212, 220 in a superior-inferior direction maximize patellar bone conservation in critical areas for, inter alia, soft tissue attachment and minimizing the risk of soft tissue detachment. While a patellar implant with a non-planar articulating surface having a concave profile in a medial-lateral direction and a convex profile in a superior-inferior direction is described herein, other embodiments may have non-planar articulating surfaces with convex and concave profiles in multiple directions to size and shape patellar implants for rigidity and bone preservation. Patellar implant 200 can also be provided with an articular surface having an elliptical-shaped portion as more fully described above in patellar implant 100.

Figures 12, 13, 14:
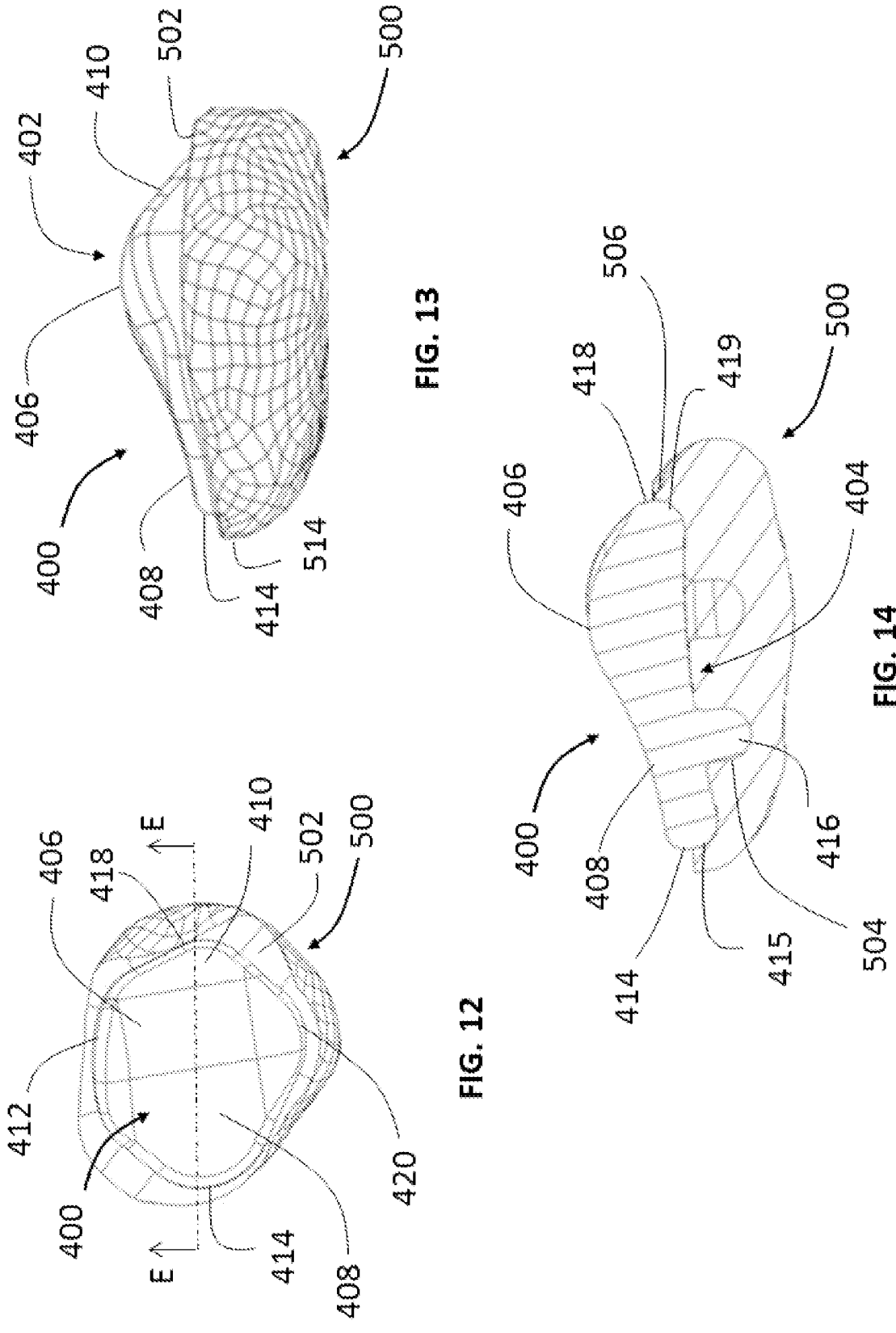
FIG. 12 is top assembled view of a patellar implant coupled to a resected patella according to a yet another embodiment of the present invention.
FIG. 13 is a side view of the patellar implant and resected patella of FIG. 12.
FIG. 14 is a cross-sectional view along line E-E of the patellar implant and resected patella of FIG. 12.

Referring now to FIG. 12, there is shown a patellar implant 400 according to another embodiment of the present invention. Patellar implant 400 has a posterior articular surface 402 with a median ridge 406 positioned between a lateral facet 408 and a medial facet 410. An opposite anterior surface 404 (FIG. 14) is configured to contact a resected patella 500. Articular surface 402 of patellar implant 400 is smaller than resected patella surface 502 leading to patellar implant undercap. FIG. 13 shows a side elevation view of patellar implant 400 secured to resected patella 500. Patellar implant undercap is further illustrated in FIG. 13 wherein a lateral peripheral edge 514 of resected patella 500 extends beyond a lateral peripheral edge 414 of patellar implant 400.

FIG. 14 shows a cross-sectional view of patellar implant 400 along line E-E of FIG. 12. Patellar implant 400 is secured to resected patella by two attachment features. The first attachment feature utilizes an onlay technique whereby one or more posts 416 extending from anterior surface 404 are received and secured in corresponding recesses 504 located in resected patella surface 502. Posts 416 enable patellar implant 400 with shear resistance parallel to the bone interfacing surface with patella 500. The second attachment feature is an inlay or inset technique whereby a footprint of articular surface 402 of patellar implant 400 is carved into resection patella surface 502. The carved foot print is slightly smaller or substantially the same size as articular surface 402 such that patellar implant 400 is press-fitted onto resected patella 500. The depth of the carved foot print is less than the height of the peripheral edges of patellar implant 400 such that patellar implant is countersunk within carved recess when secured to resected patella surface 500.

As best shown in FIG. 14, the lateral peripheral edge of patellar implant 400 is partially embedded within resected patella 500 as indicated lateral edge 415. Similarly, a portion 419 of the medial peripheral edge is also embedded within resected patellar 500. Thus, an anterior portion of patellar implant 400 is completely surrounded and encased by a bony boundary formed within patella 500. This inlay technique reduces the patella bone removal whereby bone removal is limited to the footprint of the patellar implant and not the entire patella surface as in the onlay technique. The dual attachment features incorporating both onlay and inlay techniques to secure patellar implant 400 to resected patella 500 ensures that the patellar implant is firmly secured to resected patella while simultaneously maximizing patella bone preservation.

Figures 14A, 14B, 15A, 15B:
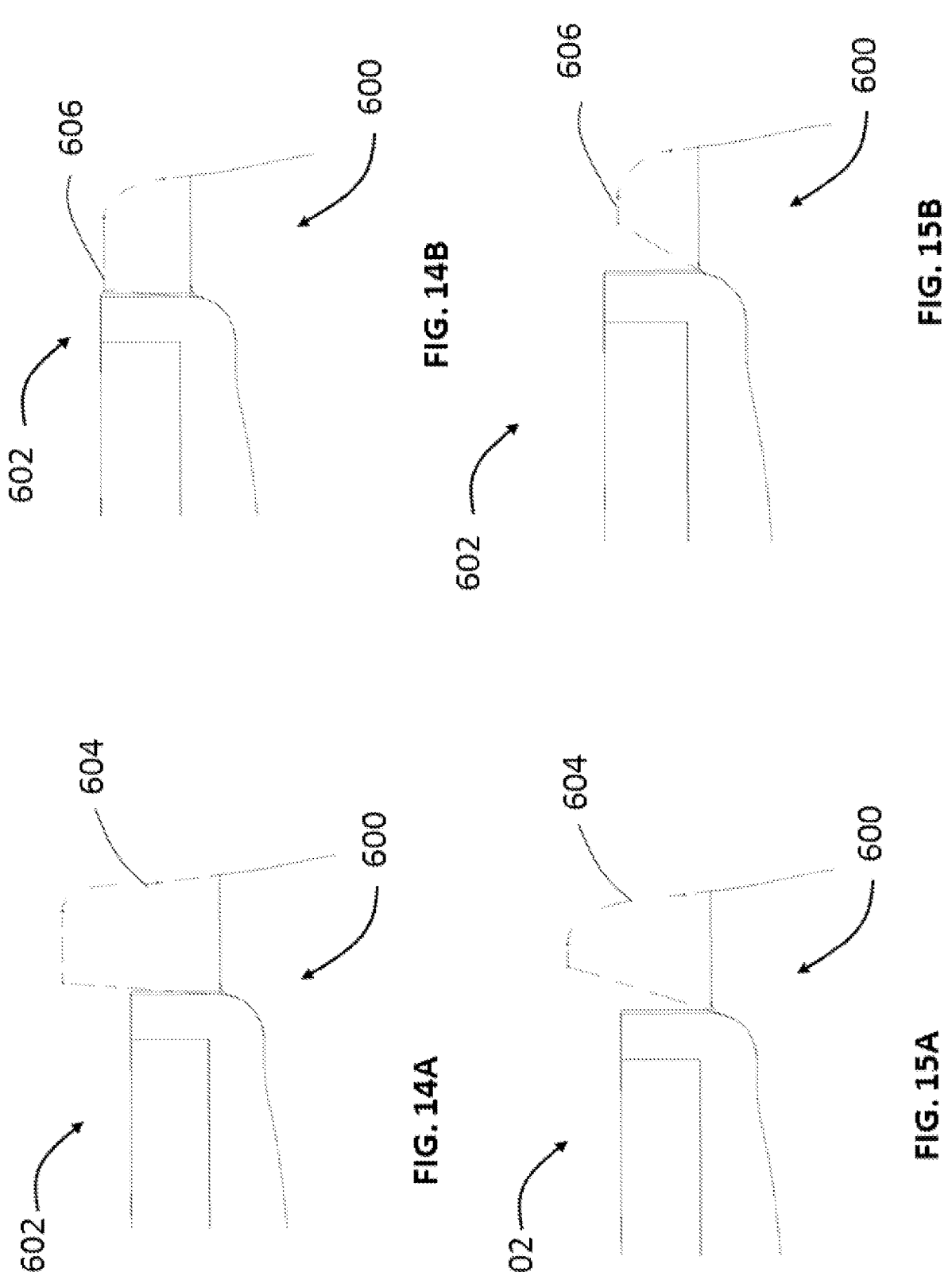
FIGS. 14A and 14B are schematic illustrations of bone preparation according to yet another embodiment of the present invention.
FIGS. 15A and 15B are schematic illustrations of bone preparation according to yet another embodiment of the present invention.

Other aspects of the present invention are methods for bone preparation to minimize the risk of implant damage and/or soft tissue impingement by resected bone surfaces. Referring now to FIGS. 14A and 14B, there is shown a first method of bone preparation. Bone resection 602 performed on native bone 600 to allow for implantation of prosthesis such as patellar implant 400 described above generally result in sharp, jagged bone edges 604. Bone edges 604 may damage implanted prosthesis (not shown) secured to bone resection 602. After performing the resection, bone edges 604 and other sharp corners are machined off by filing or other such machining processes to form a smooth prosthesis-bone surface 606 shown in FIG. 14B. FIGS. 15A and 15B show a second embodiment of this aspect wherein bone edges 604 are machined to a height below the height of the implant and contoured to provide a smooth profile for soft tissue attachment across the implant and boney surface. Although a patellar implant is used herein, this method may be utilized in any bone preparation procedures involving implanting prosthesis to resected bone.

Figure 16:
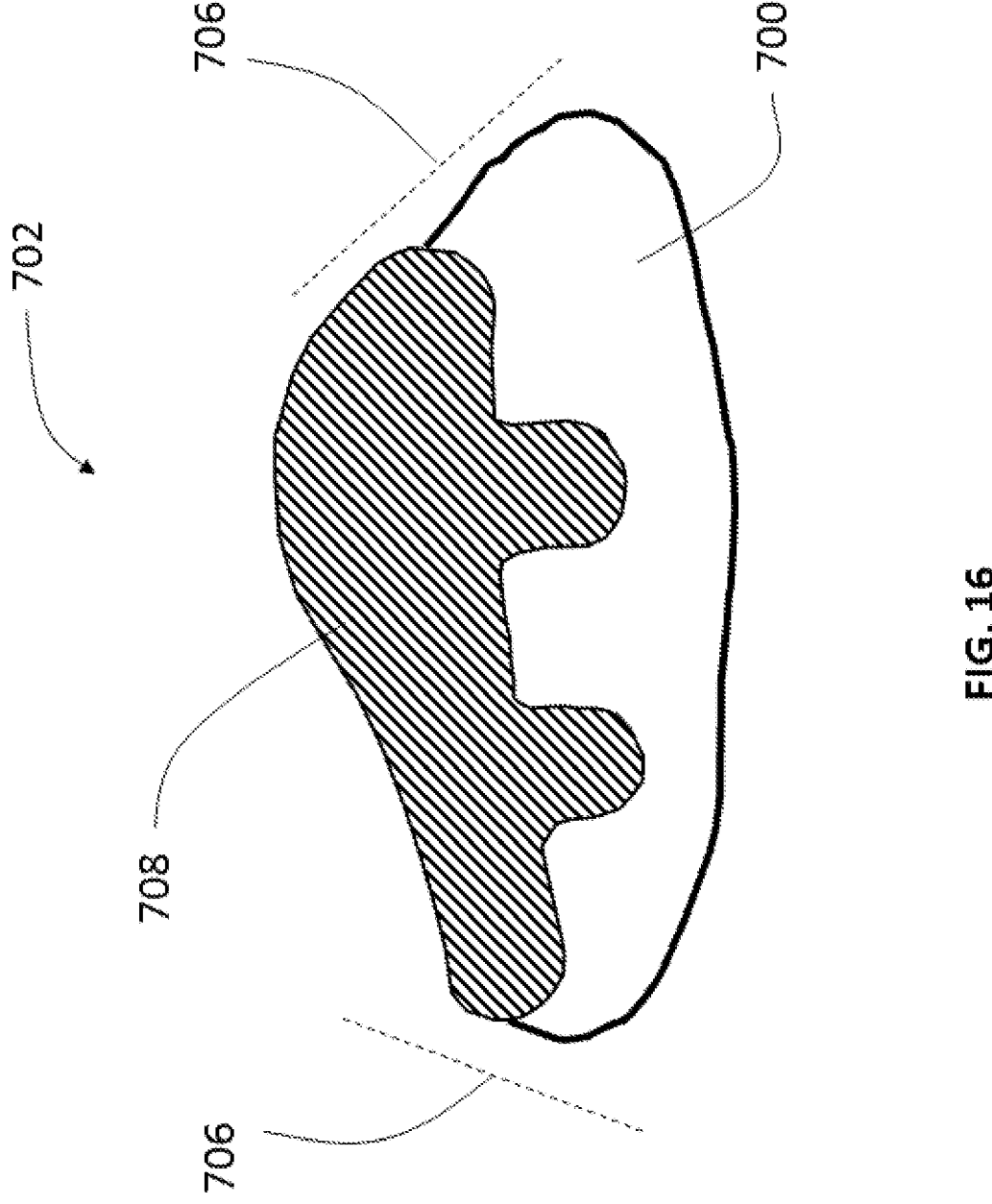
FIG. 16 is a schematic illustration of bone preparation according to yet another embodiment of the present invention.

FIG. 16 shows a method for bone preparation 702 according to another aspect of the present invention. Native bone 700 is resected to match the outer contours of implant 708 as best shown by bone-implant contour lines 706. Thus the articular surfaces of implant 708 and native bone 700 blend smoothly to form a generally continuous surface for smooth articulation with a corresponding bone or implant surface (not shown).

While a patellar implant is described these embodiments, elliptical-shaped pivoting surfaces of the present invention may be used with any implant that articulates with natural bone or another implant. Implants described herein may be made from polymers such as PEEK, carbon fiber reinforced PEEK, PAEK, UHMWPE, metals, ceramics, combinations of the foregoing, or other suitable materials that are biocompatible and possess sufficient strength and rigidity. Additive manufacturing techniques such as 3D printing may be used to fabricate implants of the present invention. Implants may also be made of composite materials. For example, the implant may have a metal base enveloped in a polyethylene or other similar material layer. The metal base may include porous regions to contact resurfaced native bone and strengthen fixation between the implant and the native bone. The polyethylene layer may be attached by compression molding or other similar means to allow the polyethylene layer to penetrate the porous regions of metal base and thereby minimize dislocation of the polyethylene layer from the metal base.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A patellar implant comprising:
a posterior surface for engaging a femoral body;
an anterior surface for engaging a resected portion of a patellar bone, the anterior surface being non-planar, and
at least one post extending from the anterior surface configured to engage with a corresponding recess in the patellar bone,
wherein the anterior surface being non-planar is such that a thickness of the patellar implant varies along an axis in a medial-lateral direction, the thickness being defined by a distance between the anterior and posterior surfaces, the posterior surface including a median ridge offset from a center of the axis along the medial-lateral direction, the median ridge defining a substantially flat surface extending between a lateral facet and a medial facet of the posterior surface.

2. The patellar implant of claim 1, wherein the anterior surface defines a convex profile along a superior-inferior axis.

3. The patellar implant of claim 2, wherein the implant thickness is greatest at a central region of the superior-inferior axis.

4. The patellar implant of claim 2, wherein the implant thickness is greatest at a central region of a medial-lateral axis of the convex profile.

5. The patellar implant of claim 1, wherein the anterior surface defines a concave profile along a medial-lateral axis.

6. The patellar implant of claim 5, wherein the anterior surface further defines a convex profile along a superior-inferior axis.

7. The patellar implant of claim 5, wherein the implant thickness is the greatest at a central region of the medial-lateral axis.

8. A patellar implant comprising:

an anterior surface for engaging a resected surface of a patellar bone;

a posterior articulating surface for engaging a femoral body;

a side wall between the anterior and posterior surfaces; and at least one post extending from the anterior surface configured to engage with a corresponding recess in the patellar bone, wherein a first portion of the side wall is configured to be countersunk within the patellar bone and a second portion of the side wall extends away from the patella when the post is received in the corresponding recess of the patellar bone, the posterior surface including a median ridge offset from a center of the axis along the medial-lateral direction, the median ridge defining a substantially flat surface extending between a lateral facet and a medial facet of the posterior surface.

9. A method for implanting a patellar implant, comprising the steps of:

resecting a posterior surface of a patellar bone to create a resection surface corresponding to an anterior surface of a patellar implant according to claim 8;

removing patellar bone on the resecting surface to create a recess corresponding to the footprint of the anterior surface of the patellar implant, a depth of the recess being less than a height of one or more side walls of the patellar implant and the footprint of the recess being substantially the same or smaller than the footprint of the anterior surface such that the patellar implant can be secured in the recess;

removing patellar bone from a surface of the recess to create one or more openings to receive the one or more posts extending from the anterior surface of the patellar implant; and placing the anterior surface of patellar implant on the recess of the patella such that the one or more posts of the patellar implant are received in the corresponding openings and patellar implant is secured in the recess such that a first portion of the side wall is countersunk within the patella and a second portion of the side wall extends away from the patella.

10. The method of claim 9, wherein the step of removing patellar bone on the resection surface to create a recess further comprises the step of machining edges of the recess to remove bone fragments to provide a smooth patellar implant to patellar bone transition.

11. The method of claim 10, wherein the smooth patellar implant to patellar bone transition forms an articulating surface.

12. The method of claim 9, wherein the patellar implant is secured to the recess by press-fitting or cementing the patellar implant to the recess.

* * * * *